United States Patent [19]

Pinkel et al.

[11] Patent Number: 5,982,534
[45] Date of Patent: Nov. 9, 1999

[54] SPECIMEN ILLUMINATION APPARATUS WITH OPTICAL CAVITY FOR DARK FIELD ILLUMINATION

[75] Inventors: Daniel Pinkel; Damir Sudar, both of Walnut Creek; Donna Albertson, Lafayette, all of Calif.

[73] Assignee: The Regents of the University of California, Oakland, Calif.

[21] Appl. No.: 08/878,145

[22] Filed: Jun. 18, 1997

[51] Int. Cl.$^6$ ............................ G02B 21/06; C07H 21/04; G01N 21/00; C12Q 1/68
[52] U.S. Cl. ........................... 359/387; 359/391; 359/396; 536/23.1; 536/24.3; 435/6; 422/50
[58] Field of Search .................... 435/287.2, 6; 536/23.1, 536/24.3, 24.37, 25.1; 359/368, 391, 396, 398, 387, 363, 372, 670, 671, 850; 422/50

[56] References Cited

U.S. PATENT DOCUMENTS

| | | | |
|---|---|---|---|
| 2,039,219 | 3/1936 | Hausser et al. | 88/40 |
| 3,432,275 | 3/1969 | Unger | 23/292 |
| 3,705,000 | 12/1972 | Guerra | 356/246 |
| 3,879,106 | 4/1975 | McCormick | 350/95 |
| 4,896,966 | 1/1990 | Boisseau et al. | 356/442 |
| 4,906,083 | 3/1990 | Sattler | 350/524 |
| 5,033,834 | 7/1991 | Corder et al. | 350/529 |
| 5,315,375 | 5/1994 | Allen | 356/417 |
| 5,326,398 | 7/1994 | Kelley et al. | 118/52 |
| 5,417,576 | 5/1995 | Hill | 435/299 |
| 5,545,561 | 8/1996 | Lleonart Alibertas | 439/287.3 |
| 5,665,599 | 9/1997 | Minuth | 435/288.3 |

OTHER PUBLICATIONS

Killioniemi et al., *Science* 258:818–820 (1992).
Fodor et al., *Science* 251:767–773 (1991).
Sheldon et al., *Clinical Chemistry* 39(4):718–719 (1993).
Kozal et al., *Nature Medicine* 2(7):753–759 (1996).
Wittrup, et al., Fluorescence Array Detector for Large–Field Quantitative Fluorescence Cytometry, Cytometry 16:206–213 (1994).

*Primary Examiner*—Kenneth R. Horlick
*Assistant Examiner*—Jeffrey Siew
*Attorney, Agent, or Firm*—Townsend and Townsend and Crew LLP

[57] ABSTRACT

An illumination apparatus with a specimen slide holder, an illumination source, an optical cavity producing multiple reflection of illumination light to a specimen comprising a first and a second reflective surface arranged to achieve multiple reflections of light to a specimen is provided. The apparatus can further include additional reflective surfaces to achieve the optical cavity, a slide for mounting the specimen, a coverslip which is a reflective component of the optical cavity, one or more prisms for directing light within the optical cavity, antifading solutions for improving the viewing properties of the specimen, an array of materials for analysis, fluorescent components, curved reflective surfaces as components of the optical cavity, specimen detection apparatus, optical detection equipment, computers for analysis of optical images, a plane polarizer, fiberoptics, light transmission apertures, microscopic components, lenses for viewing the specimen, and upper and lower mirrors above and below the specimen slide as components of the optical cavity. Methods of using the apparatus are also provided.

34 Claims, 3 Drawing Sheets

SPECIMEN ILLUMINATION APPARATUS WITH OPTICAL CAVITY FOR DARK FIELD ILLUMINATION

STATEMENT OF GOVERNMENT SUPPORT

This invention was made with Government support under Grant No. NIST-W-7405-ENG-48, awarded by the Department of Energy and Grant No. CA45919 and HD17665, awarded by the National Institutes of Health. The Government has certain rights in this invention.

FIELD OF THE INVENTION

The present invention provides specimen illumination apparatus and methods of use. The illumination apparatus provides an optical cavity for illuminating a sample viewed by light scattering in dark field illumination, or viewed by fluorescence.

BACKGROUND OF THE INVENTION

Microscope illumination systems direct light onto a specimen and create "bright field" or "dark field" illumination. Bright field illumination is so named because light rays passing through the field surrounding the specimen and entering the microscope objective lens are unimpeded and thus bright compared to light rays attenuated by passing through the specimen. In contrast, in a "dark field" system, the relative brightness is reversed for the viewer by directing light rays onto the specimen field at an angle which falls outside the objective viewing aperture. The light passing through the specimen field surrounding the specimen is unimpeded and not observable through the objective lens of the microscope. However, some of the light directed onto the specimen is scattered and enters the viewing objective. Thus, the specimen appears brighter than the surrounding dark field.

Similarly, in fluorescence-based microscopy, light is typically directed into the specimen field at an angle which minimizes the amount of illumination light that enters the observation optics, for example it passes through the optics in a direction opposite to the light path of the observer. Use of filters to remove remaining stray illumination and scattered light makes the field appear dark to an observer. Excitation of fluorophores in the fluorescent sample give off secondary light, making the specimen appear bright. In a typical application, the illumination light passes through the specimen only once.

One use for fluorescence-based microscopy is the detection and quantification of inorganic, organic and biological polymers. Fluorescence is analyzed in clinical settings to obtain measurements in connection with immunology, toxicology, microbiology, drug screening, clinical chemistry, histopathology, and the like. Fluorescence is analyzed in many contexts to study enzymes, amino acids, carcinogens, and a wide variety of other chemical compounds. Nucleic acids such as DNA and RNA, proteins, chromosomes and other macromolecular structures are all visualized by fluorescence-based microscopy. Arrays of biological polymers are monitored by fluorescence-based microscopy for nucleic acid sequencing by hybridization, detection of genetic polymorphisms, drug screening and many other uses. For instance, comparative genomic hybridization (CGH) is a well-known approach for identifying the presence and localization of amplified or deleted sequences in a genome compared to a reference genome. See, Kallioniemi, et al. (1992) *Science* 258:818 and Pinkel et al. PCT/US95/16155 (WO 96/17958). CGH reveals amplifications and deletions irrespective of genome rearrangement and is used, e.g., for cancer assessment and diagnosis by monitoring amplifications or deletions associated with various cancers. CGH can provide a quantitative estimate of copy number and also provides information regarding the localization of amplified or deleted sequences in a normal chromosome.

Another increasingly useful florescence-based technology provides high density arrays of biological polymers on substrates, typically hundreds to thousands to tens of thousands of distinct polymers per square cm. This permits screening of thousands of different molecular interactions simultaneously. For example, very large scale immobilized polymer arrays (VLSIPS™ arrays) are used for the detection of nucleic acids for a variety of purposes. See, Fodor et al. (1991) *Science*, 251: 767–777; Sheldon et al. (1993) Clinical Chemistry 39(4): 718–719 and Kozal et al. (1996) *Nature Medicine* 2(7): 753–759. See also, Pinkel et al. PCT/US95/16155 (WO 96/17958). Analysis of these arrays requires high sensitivity quantitative fluorescence measurements covering areas of typically one to several $cm^2$.

Conventional fluorescence microscopes and laser scanning microscopes are suitable for such measurements, but they acquire results slowly because they only examine a small region on the substrate at one time. Conventional microscopes are also limited by the passage of excitation light through the same lens that collects the fluorescence for the specimen. This produces autofluorescence in the lens that interferes with the ability to observe weak signals.

The present invention solves these and other problems by providing apparatus and methods for illuminating large areas at one time such that illumination light makes multiple passes through the specimen, thereby increasing signal intensity. The illumination light does not enter the observation optics, minimizing optical "noise" in the system.

SUMMARY OF THE INVENTION

The present invention utilizes light reflective surfaces such as mirrors and/or total internal reflection to form an optical cavity around a specimen providing high intensity illumination of the specimen in a manner which keeps illumination light from entering the optics which are being used to observe the specimen. Uses for the invention include, but are not limited to, dark field microscopy and fluorescence microscopy. An advantage of the invention over prior art illumination systems is that signal intensities are increased enough that less expensive and less specialized illumination sources and detectors can be used to monitor a sample. Another advantage is that excitation light is excluded from the detection optics, providing a dark field view of a florescent sample, thereby increasing the signal to noise ratio for detection of fluorescent samples. An additional advantage is that relatively large areas can be viewed at once, providing for the ability to monitor simultaneously a large arrays of materials.

The invention provides an illumination apparatus for viewing a specimen. The apparatus is constructed to have a specimen slide holder for mounting a specimen slide. The slide holder has a specimen viewing region. A light source provides light to an optical cavity surrounding a portion of the specimen viewing region (the specimen viewing region includes the region from any specimen to be viewed to the observation optics, including the region in which the specimen is located). The optical cavity can include all of the specimen viewing region, or only a small portion of the specimen viewing region, e.g., just the portion of the region comprising a sample.

The optical cavity has reflective surfaces which multiply reflect light from the light source, thereby illuminating the specimen viewing region. In some preferred embodiments, the apparatus includes the specimen slide, and, optionally, the specimen. The slide is mounted in, on, or by the slide holder, which is optionally a simple platform, or can include more specialized components such as a slide holding armature, orifices for introducing light or viewing a specimen, or the like.

The specimen slide has a specimen side, a light receiving side and a specimen positioned on its specimen receiving side. In one group of embodiments, the specimen side and the light receiving side of the slide are the same, while, in other embodiments, the light receiving and specimen sides are on opposite sides of the slide. The specimen may be covered, for example, with a mounting medium and coverslip. Light from the illumination source propagates in a manner which prevents direct entry of the illumination light into any detection device. Some scattered or ambient light optionally enters the detection optics; filters are optionally used to reduce unwanted light from the detection optics in either fluorescent or dark field embodiments.

In some embodiments, total internal reflection from the coverslip or slide contributes to the formation of the optical cavity. Optionally, a portion of the coverslip or slide has a reflective coating. Prisms are optionally mounted on the specimen side of the specimen slide, or, optionally, on a side opposite the specimen. These prisms direct light against reflective surfaces which form the optical cavity, or direct light through or along the specimen slide.

In some embodiments, the optical cavity includes a first reflective surface, a second reflective surface a third (and, optionally, fourth, fifth, sixth or more) reflective surface and light is multiply reflected by the surfaces, making multiple passes through the specimen.

In one embodiment, the prism is mounted on the light receiving side of the specimen slide, e.g., using an immersion oil. Light enters the prism, passes thought the specimen and undergoes total internal reflection at the surface of the coverslip. It then passes back through the specimen and prism. The light is then reflected back toward the specimen by a second reflective surface, reflected by the coverslip again, passes through the sample again and into the prism. This light is once again reflected back towards the specimen by a third reflective surface, whereby the sequence repeats. The resulting multiply reflected light illuminates the specimen.

In one embodiment, an apparatus of the invention includes a slide with a light reflecting specimen side which includes the first reflective surface. In this embodiment, the apparatus includes a coverslip covering a portion of the light reflecting specimen side of the specimen slide, and, optionally, a specimen positioned on the light reflecting specimen side of the specimen slide, or the side opposite the light reflecting side. Placing the specimen on a reflective surface increases the amount of fluorescence from the specimen that reaches the detector. A first prism mounted on the light reflecting specimen side of the specimen slide directs light from the light source against the light reflecting specimen side of the specimen slide, which reflects a portion of the light against the coverslip, which reflects light by total internal reflection against the light reflecting side of the specimen side of the specimen slide, thereby illuminating the specimen with multiply reflected light. In one embodiment, a second prism is mounted on the light reflecting specimen side of the specimen slide, which directs multiply reflected light against a first mirror. The first mirror reflects the multiply reflected light back through the second prism and against the light reflecting specimen side of the specimen slide, where the multiply reflected light is multiply reflected between the light reflecting specimen side of the specimen slide and the coverslip, thereby further illuminating the specimen. In one particular embodiment, the apparatus further includes a second mirror mounted to reflect the multiply reflected light from the first prism back through the first prism against the light reflecting specimen side of the specimen slide, where the multiply reflected light is reflected between the light reflecting specimen side of the specimen slide and the coverslip, thereby further illuminating the specimen. The second mirror optionally includes a light transmission aperture which permits light from the light source to pass through the aperture.

Also provided are methods of illuminating a specimen viewing region. In the methods, an apparatus with any of the component parts described, e.g., above is provided. In one class of preferred embodiments, the methods and apparatus of the invention provide dark field illumination of the sample. In one embodiment, the methods provide for fluorescence of the sample by directing light to the sample at an angle which does not substantially enter the field of view of the observation optics.

The methods of the invention optionally include focusing a lens to view an optical image of the specimen. In a preferred embodiment, the image is viewed at low magnification, providing for the ability to view a relatively large image. Any optical image is optionally photographed, digitally recorded, or the like. Computers are optionally used to analyze digitized images of a specimen. In embodiments where arrays are viewed, the methods optionally further include hybridizing materials to the arrays such as nucleic acid or protein probes.

DEFINITIONS

Figure 1:
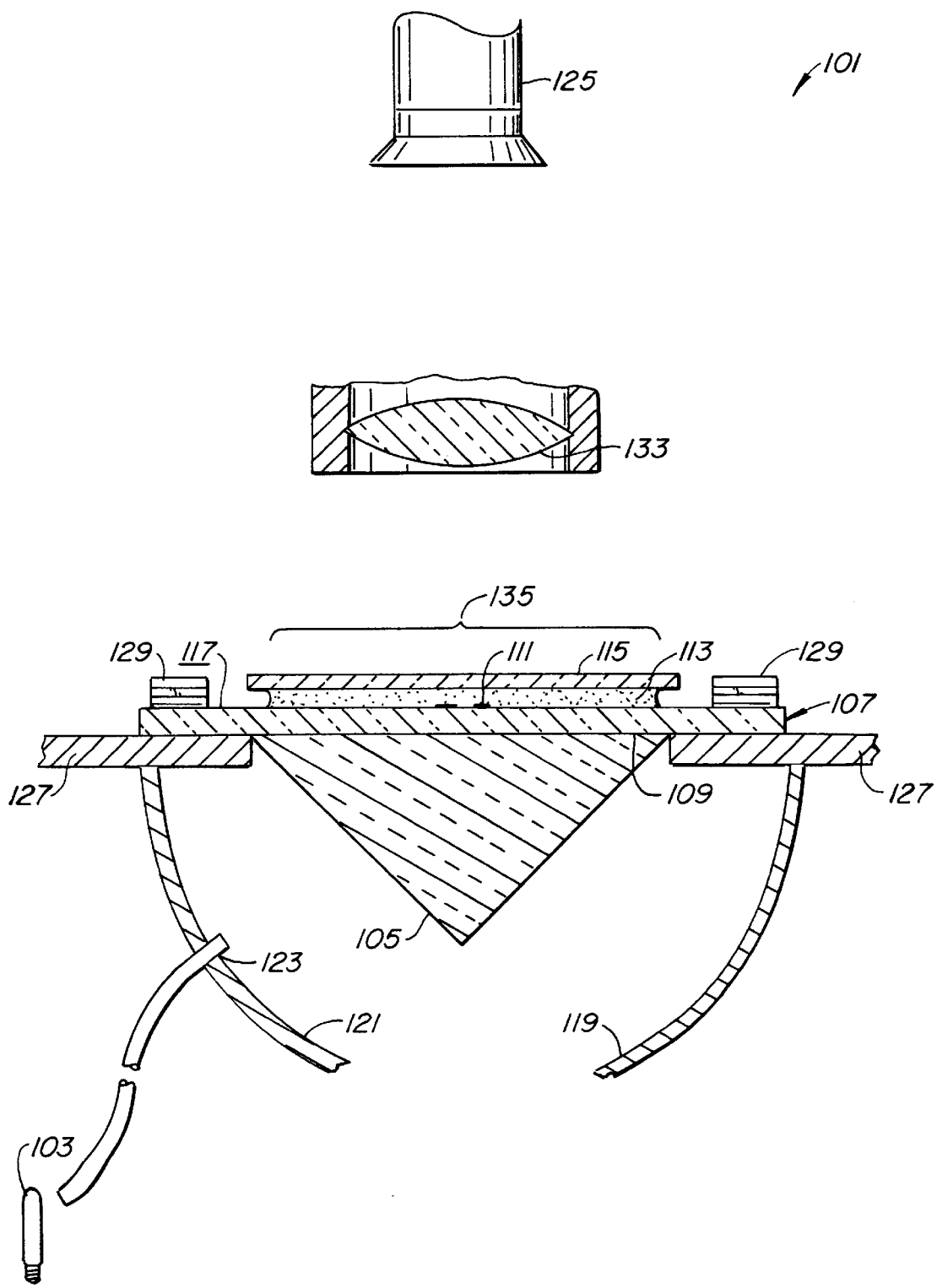
FIG. 1 is an illustration of an embodiment of the invention showing an optical cavity for dark field illumination or illumination of a florescent specimen.

An "optical cavity" is a reflective structure which has reflective surfaces directing light to have multiple reflections between the surfaces. Ordinarily, at least a majority of the light delivered to an optical cavity is reflected within the optical cavity. A simple example optical cavity is a sphere having a reflective inner surface with a light delivery orifice. Light delivered to the sphere through the orifice is reflected within the sphere. Similarly, other structures such as top and bottom mounted reflective surfaces are positioned to multiply reflect illumination light to create an optical cavity. A light ray is "multiply reflected" when it is reflected from more than one reflective surface, or is reflected from more than one location on a continuous reflective surface such as the sphere described above.

A "reflective surface" is a substrate comprising a face which reflects a substantial portion of light directed against the face. In some embodiments, the reflective surface is mirrored, i.e., coated with a finish which reflects substantially all of the light directed against the face. In other embodiments, the face is substantially reflective only to light which is directed against the surface at a particular angle (e.g., a glass coverslip allows light to pass through the coverslip at some angles, and reflects light delivered against the cover slip at other angles). A reflective surface is "substantially reflective" when the surface reflects at least 50%, preferably at least 60%, often at least 70%, generally at least 80%, usually at least 90% and optionally as much as 99% or more of the light directed against the surface at a specified angle, and optionally with a selected wavelength.

A "specimen" is a sample of material to be viewed. The specimen can be made of any material which a viewer wishes to view using a light-based viewing technique such as microscopy or photography. Examples include molecular structures such as those made from a biological polymer (RNA, DNA, lipid, or protein, or a combination thereof, such as a chromosome, ribosome, membrane or the like), partial or whole organelles or cells, tissues, organs, arrays of chemical or biological polymers or other materials (e.g. where the arrays are attached to viewing substrates such as a slide or bead), small physical structures such as transistors or arrays of transistors, and the like. A specimen optionally includes a coverslip, dye or anti-fading solutions and the like which facilitate viewing.

A "specimen slide" is a substrate for mounting a specimen for observation. The substrate can be made from a variety of materials, including glass and other silicates, plastics, and metals. The substrate is optionally planar (e.g., where the slide is a typical flat glass microscope slide), but other arrangements, wherein the substrate comprises grooves, wells, depressions, walls and the like are also suitable.

A "specimen viewing region" is a portion of space proximal to the specimen through which the specimen can be viewed by an observer.

A "coverslip" is a substrate which covers a portion (or all) of the specimen. The substrate can be made from a variety of materials, including glass and other silicates, transparent plastics and the like. Coverslips are typically planar (e.g., where the coverslip is a flat piece of glass or plastic), but other arrangements, e.g., wherein the substrate comprises grooves, wells, depressions, walls and the like are also contemplated. At certain angles, light is reflected by the coverslip. In these embodiments, the coverslip is part of the optical cavity which surrounds the specimen.

A "specimen holder" is a device suited to support a specimen slide. It will be appreciated that the precise conformation of the holder is optionally adapted to the shape of the slide. As slides are optionally of any regular or irregular geometric shape, such as square, rectangular, circular, or the like, the holder is optionally adapted to support the particular shape of slide. Typical holders have a platform for supporting a slide (although this is optionally omitted), and optionally further comprise a grasping armature, a cover or the like.

An "array" of materials refers to a set of materials with a known location on a substrate. Although optionally placed into a regular arrangement to facilitate analysis (rows, columns, geometric patterns, or the like), the array can be any arrangement, as long as the approximate location of materials on the substrate is known.

A "camera" is any device which records an optical image. This includes conventional still and video film cameras, charged coupled devices, digital cameras, phototubes linked to recording devices, and the like.

"Total internal reflection" refers to the ability of the surface of an object with a high index of refraction relative to its surroundings to reflect light when the light hits the surface with a large enough angle. For example, FIG. 1 describes an optical cavity made, in part, by reflection of light from a coverslip due to total internal reflection.

"Illumination light" refers to light which illuminates a specimen, including excitation light delivered to an optical cavity from a light source, and reflected light which is reflected one or more times within an optical cavity of the invention.

A "prism" is an optical component which has an index of refraction different than its surroundings. A prism is optionally made from a material such as glass, quartz, crystal or plastic and optionally can have a reflective coating over a portion of the prism, e.g., on one or more of its surfaces, to form a portion of an optical cavity.

When a feature of an apparatus of the invention is indicated to be "above" or "below" another feature, it will be appreciated that this is with reference to an observation point such as the observation optics, which is arbitrarily considered to be either above or below a specimen. For example, although the apparatus of FIG. 1 is optionally mounted in any orientation (top-down, side-to-side, etc., with the specimen slide parallel, perpendicular or at an angle relative to actual vertical) with respect to a center of gravity, the observation optics can arbitrarily be considered to be above the specimen.

DETAILED DESCRIPTION OF THE INVENTION

Improved techniques for excluding excitation light from a viewing lens or aperture while increasing the light produced by fluorescence or scattering by a specimen are desirable, because they result in improved signal to-noise ratios for a viewer. This improved signal to-noise ratio permits quantitation of smaller samples and simplifies automation of detection of specimens. This invention provides substantially improved signal-to-noise viewing ratios. In particular, the invention includes optical cavities which multiply reflect light from a light source to a sample, thereby substantially amplifying the light used to illuminate the sample. This amplification reduces the amount of light needed from a light source, making it possible to use less expensive light sources for illuminating samples. Similarly, it permits efficient illumination of large areas of a specimen.

Samples which are illuminated can include any material which is optically observable. In particular, the invention provides improved dark field microscopy and photography, in which the specimen scatters illumination light, and improved fluorescence based microscopy and photography.

The present invention is illustrated by consideration of FIG. 1, depicting illuminated illumination apparatus 100 for viewing a specimen, comprising optical cavity 101, although one of skill will immediately recognize that alternative arrangements are also possible and equally preferred.

Light source 103 directs excitation light through prism 105 where the excitation light is directed through specimen slide 107. Optionally, prism 105 is mounted on light receiving face 109 of specimen slide 107. Mounting means include immersion oils, adhesives and the like. Alternatively, specimen slide 107 and prism 105 can be integral, e.g., cast from a single piece of glass or optical plastic. The slide and prism are considered integral when the slide and prism are permanently adhered to one another, e.,g., by thermal bonding, formation in a single mold, or using an adhesive.

The excitation light travels through specimen slide 107 and illuminates specimen 111. Optionally, as illustrated, specimen 111 comprises antifade solution 113 and a first reflective surface such as coverslip 115, which reflects light back through specimen 111 by total internal reflection. Specimen 111 and specimen slide 107 are optionally integral, e.g., where the specimen is linked (covalently or non-covalently) to the specimen slide. An example of this embodiment is the association of a nucleic acid, nucleic acid array, protein, protein array, chromosome, biological cell, electrical transistor, or the like, to slide 107. Similarly, any of the specimens described herein are optionally integral with any of the slides for mounting specimens which are described herein. Many examples of chemistry for attaching polymers to glass or plastic substrates used as slides are known. for example, silane chemistry can be used for the attachment of nucleic acids and other biopolymers to glass slides. See, e.g., Fodor et al. (1991) *Science*, 251: 767–777; Sheldon et at. (1993) Clinical Chemistry 39(4): 718–719 and Kozal et al. (1996) *Nature Medicine* 2(7): 753–759 PCT patent publication Nos. WO 90/15070 and 92/10092 and Pirrung et al., U.S. Pat. No. 5,143,854.

The excitation light is reflected off of coverslip 115 by total internal reflection, thereby becoming reflected light. The reflected light is transmitted back through specimen 111, passing through specimen side 117 of specimen slide 107 and subsequently through prism 105. Upon exiting prism 105, the reflected light is reflected from a second reflective surface such as mirror 119, back through prism 105 and specimen slide 107, where the reflected light further illuminates specimen 111. The reflected light is again reflected from cover slip 115, back through specimen slide 107 and prism 105, where the reflected light is reflected from a third reflective surface such as mirror 121, back through prism 105 and specimen slide 107, where it illuminates specimen 111, etc.

Illumination light (i.e., light which illuminates the specimen, including both excitation light from a light source and light reflected in the optical cavity) thus makes many passes through the specimen until it is either absorbed or escapes from the cavity by scattering, or otherwise escapes from optical cavity 101. The only unwanted scattered light which enters the detection optics is scattered light which hits the surface of coverslip 115 at an angle that does not result in total internal reflection, for example where illumination light which is not reflected by coverslip 115 exits the coverslip at an angle close to the plane of the coverslip.

It will be appreciated that this scattered light is minor in comparison to the total illumination light. Thus, this embodiment provides both dark field illumination to permit observation of light scattering by the specimen and fluorescence excited in the specimen. Furthermore, unwanted scattered light is optionally removed from the detection optics using appropriate filters.

Light source 103 optionally directs excitation light through mirror 121, where it is optionally mounted in light source aperture 123. Light source 103 can be any known light source, e.g., a light bulb, arc lamp, or laser, or, commonly, a combination thereof, and optionally further including means for directing the light, such as a fiberoptic cable. Alternatively, light source 103 can be a light mounted behind mirror 119, with excitation light passing through aperture 123. Alternatively, aperture 123 is omitted, and light source 103 provides light between mirrors 119 and 121, and prism 105. It will be appreciated that mirrors 119, 121 and coverslip 115 form optical cavity 101.

Mirrors 119 and 121 are shown as curved mirrors for simplicity of illustration. In a preferred embodiment, the focal length of the mirrors are approximately equal to the length of the light path between the mirrors. One of skill will recognize that in alternative embodiments, mirrors 119 and 121 are substituted with mirrors which are optionally flat, spherical, parabolic or elliptical. Although mirrors 117 and 119 are shown as separate mirrors for illustrative purposes, one of skill will appreciate that alternative arrangements in which the mirrors are optionally combined into a single mirror (e.g., a flat, toroidal, hemispherical or hemielliptical mirror) are also possible. In a preferred embodiment, mirrors 119 and 121 are replaced with a single contiguous toroidal mirror. In other embodiments, mirrors 119 and 121 comprise multiple connected reflective surfaces. In still other embodiments, additional mirrors are located between mirrors 119 and 121 under the prism to collect and reflect additional light. Similarly, additional reflective surfaces are optionally used to direct fluorescent light emitted by specimen 111 or light scattered by specimen 111 to a set of detection optics. For example, in one embodiment, a mirror directs fluorescence emitted by a specimen back towards detection optics. In one embodiment, prism 105 and mirrors 119 and 121 are substituted with an integral, or partially integral prism-mirror arrangement, e.g., where a prism comprises an inwardly mirrored face of an appropriate shape. A light source can also be made integral in this arrangement. In one arrangement, prism 105, mirrors 119 and 121 are substituted with a prism having an integral toroidal outer mirror. An advantage to the toroidal design is that reflective surfaces are continuous, providing numerous paths for reflected light that do not allow the light to escape from the cavity through light source aperture 123.

In one class of embodiments, coverslip 115 is optionally omitted, e.g., where fluorochromes in sample 111 emit light upon excitation when dry.

Illumination light illuminates the specimen as described with multiple reflections of light. As shown, the viewing apparatus optionally further comprises optical or photographic components for viewing the sample, such as objective lens 133 and, optionally, camera 125. As one of skill will appreciate, camera 125 is optionally a still film camera such as a 35mm camera, or is optionally a video, CCD, moving film camera, or the like. Other suitable detection apparatus include detectors such as phototube(s), photodiode(s), a charge coupled device, a spectrophotometer, or the like. In a preferred embodiment, objective lens 133 provides for low magnification of the sample. It will be appreciated that a primary use for the increased light available for specimen illumination provided by the present invention is low magnification viewing of a sample, where large areas need to be illuminated with high intensity.

Slide 107 is held in position with slide holder 127 optionally comprising an armature adapted for holding the slide in place, such as arms 129. Slide 107 is viewed through specimen viewing region 135. In this embodiment, specimen viewing region 135 extends from sample 111 upwards, to lens 133. Thus, optical cavity 101 includes a portion of specimen viewing region 135, i.e., between coverslip 115 and slide 107. Although shown as a simple platform for simplicity of illustration, slide holder 125 optionally includes arms 129 for positioning slide 107, cutout regions for bottom mounted light or power sources, detection optics, or the like, or gear arrangements for movement of the platform or sample slide. In some embodiments, the slide and slide holder are integral.

In operation, detection of fluorescent samples is provided, inter alia, by the embodiment of FIG. 1. In one particularly preferred embodiment, detection of fluorescent signals in a nucleic acid or other biopolymer) array is provided. One of skill is fully able to make arrays of biological polymers as samples, and companies which specialize in the manufacture and design of such arrays are well known. Examples include Affymax, Inc. and Affymetrix, Inc., both of Santa Clara, Calif. Additional preferred arrays, e.g., for the detection of chromosomal abnormalities by comparative genomic hybridization are described, e.g., in commonly assigned, copending application U.S. Ser. No. 08/353,018 by Pinkel et al. filed Dec. 9, 1994, attorney docket number 02307E-056100 entitled "Comparative Fluorescence Hybridization to Nucleic Acids;" see also, Pinkel et al. PCT/US95/16155 (WO 96/17958).

Detection of fluorescent signals in a nucleic acid array requires high sensitivity quantitative imaging of many target spots on the array. The resolution that is required is relatively low, so that it is attractive to design systems that can image large areas at one time, for example, 0.5 to 1 cm$^2$. Such areas can contain hundreds, thousands or even tens of thousands of individual target spots, each spot potentially including a very large number of individual molecules of the same type. In one embodiment, The target spots are located on the surface of specimen slide 107 mounted in a standard glycerol based fluorescence anti-fading solution, and covered with coverslip 115. Coverslips are commonly made from glass or quartz. The nucleic acids (or other polymers) of the array are, thus, contained in an environment with an index of refraction of about 1.5. Lens 133 used in operation, e.g., to collect fluorescence, views the array through coverslip 115. Prism 105 (made, e.g., from quartz) is mounted on the back of slide 107 (also optionally made from quartz) and coupled to the slide with immersion oil. The illumination light from illumination system 103 is directed onto one surface of prism 105. The light passes through slide 107 and the targets, into the antifade solution, and, finally, into the coverslip. The angles are chosen so that the light undergoes total internal reflection at the interface between coverslip 115 and the air. It then passes back through the specimen slide, into the prism, and through the prism. Mirror 119 reflects the light back into prism 105 and partially focuses it. The reflected light again excites the fluorophores in the target array, are reflected by total internal reflection by coverslip 115 back through the prism and against mirror 121. In this example, mirror 121 has an aperture through which light from illumination system 103 enters the apparatus. Mirror 121 reflects light back into prism 105, to the array (thereby again exciting the fluorophores in the sample), against coverslip 115, back through prism 105, and against mirror 119. The process of reflection is repeated several times, until the light is absorbed or escapes from the cavity, thereby causing the light to multiply excite the fluorophores in the array. The polarization of light in the system is optionally adjusted to minimize or maximize (depending on the application) the amount of light scattered by the specimen, or any debris.

Figure 2:
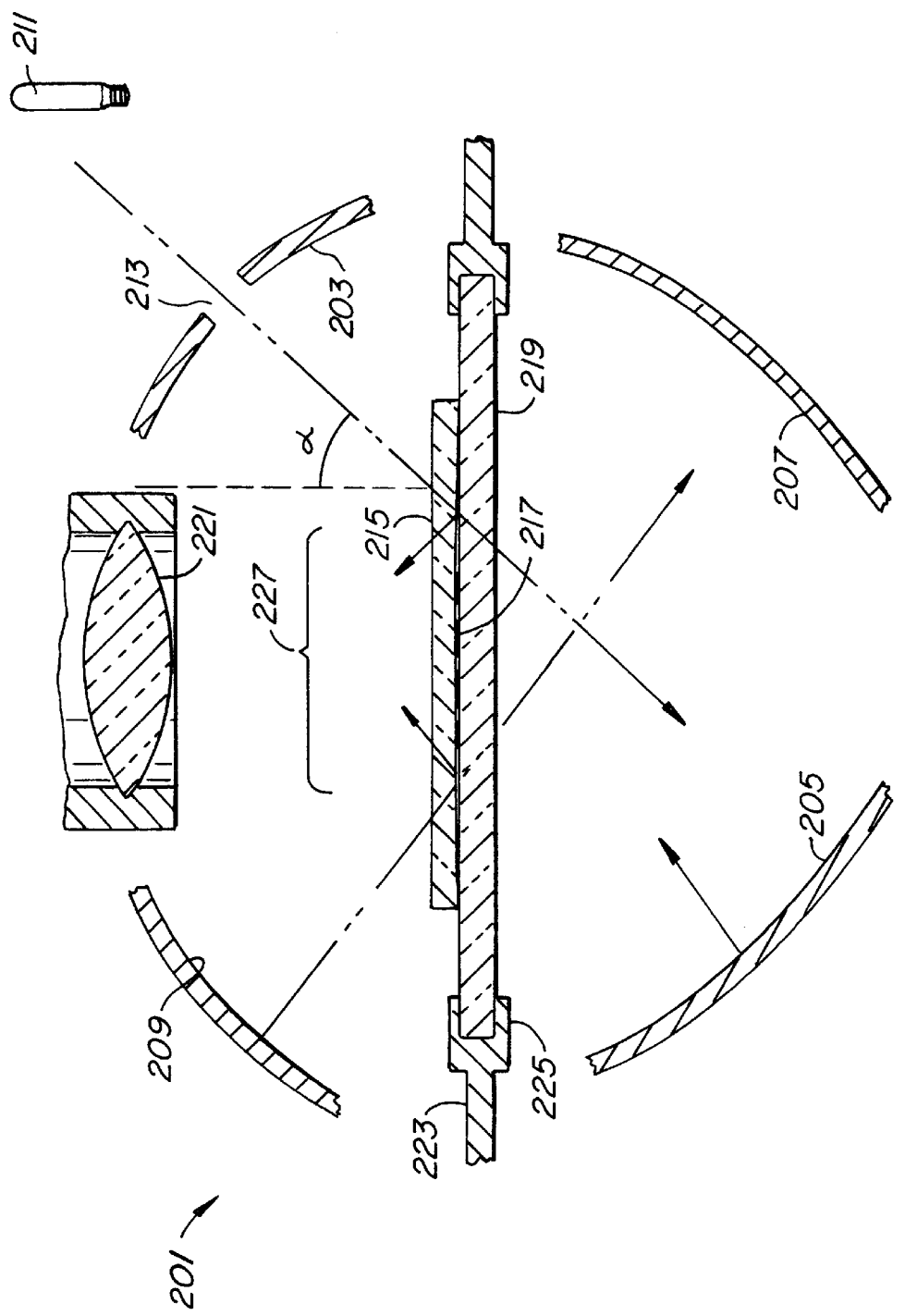
FIG. 2 is an illustration of an embodiment in which reflective surfaces above and below the plane of a sample are used.

A second preferred embodiment is illustrated in FIG. 2. Optical cavity 201 is made up of first reflective surface 203, second reflective surface 205, and, optionally, third reflective surface 207, and fourth reflective surface 209. Typically, reflective surfaces 203, 205, 207, and 209 are curved mirrors.

Input light from light source 211 enters optical cavity 201 through optical aperture 213. For simplicity of illustration, optical aperture 213 is located in reflective surface 203, but it will be appreciated that equally preferred arrangements with an aperture located in any of 203, 205, 207, or 209 are also preferred, as are arrangements with multiple light sources directing light through apertures in more than one reflective surface.

In one class of embodiments, input light from light source 211 is plane polarized. In this class of embodiments, reflective surfaces 207 and 209 are, optionally, omitted. In operation of optical cavity 201, plane polarized light from light source 211 enters optical cavity 201 through aperture 213. Input light passes through coverslip 215 which is located over sample 217, and passes through sample slide 219. Angle α (measured relative to normal to slide 203) is adjusted to Brewster's angle, permitting essentially all of input light to pass through coverslip 215 and slide 219 (it will be appreciated that a small portion of input light is absorbed or scattered by sample 217, or lost to other processes). Brewster's angle is the angle at which plane polarized light enters or exits a medium having a particular refractive index without being reflected from the surfaces. See, e.g., Jenkins and White (1976) *Fundamentals of Optics, Fourth Edition* McGraw-Hill Book Company, NY for a basic introduction to Brewster's law, as well as other optical phenomena.

Light will pass through cover slip 215 and slide 219, being refracted as it passes through coverslip 215, sample 217 and slide 219 at an angle dependent upon the index of refraction of these light transmissive materials. Input light which passes through slide 219 is reflected from second reflective surface 205, thereby becoming reflected light which passes back through slide 219, illuminating sample 217, passing through coverslip 215, and against first reflective surface 203, where it is again reflected (becoming "multiply reflected"). Detection optics 221 detects illumination light (direct input or excitation light and all reflected light which together illuminate the sample) which is scattered by sample 217, or light emitted by sample 217 due to florescence.

In another class of embodiments, the input light is not plane polarized, or α is not Brewster's angle. In this embodiment, some input light will be reflected by cover slip 215 and slide 219. Light reflected from coverslip 215, slide 219 and sample 217 is captured and reflected by additional reflective surfaces 207 and 209, back through specimen 217. Thus, optical cavity 201 is formed by reflective surfaces 203, 205, 207, and 209.

Detection optics 221 is conveniently shown above specimen 217. However, one of skill will appreciate that the detection optics are optionally placed above or below specimen 217 (and above or below coverslip 215 and slide 219). As described above, detection optics include any known lens system and recording device for monitoring optical phenomena, including, but not limited to, cameras, CCD cameras, phototubes, photodiodes, microscopes, video cameras, and any combination thereof, optionally in operable combination with a computer or other analysis system or device.

It will be appreciated that specimen 217 is optionally integral with slide 219 and/or coverslip 215, in a manner similar to that described above for other specimen embodiments. Again, as above, coverslip 215 is optionally omitted, particularly where the sample is to be viewed without benefit of a liquid medium. A prism is optionally located above or below the sample for directing light.

Although depicted with single light source 211 and a single aperture 213, it should be understood that additional light sources and/or apertures are conveniently used to increase illumination in optical cavity 201. Although reflective surfaces 203, 205, 207, and 209 are depicted as separate curved mirrored surfaces, it will readily be understood that the mirrored surfaces are optionally flat, toroidal, hemieliptical, hemispherical, etc. Further, the physical arrangement of components of the invention are varied to achieve specific results, such as focusing of reflected light, uniform illumination of the specimen, and the like. Reflective surfaces 203, 205, 207, and 209 are optionally combined into a single reflective structure, such as a spherical or toroidal mirror with apertures for viewing the sample and for introducing light into optical cavity 201. Similarly, additional reflective surfaces are optionally added between reflective surfaces 203, 205, 207, and/or 209.

Slide 219 is held in position with slide holder 223 optionally comprising arms 225. Slide 219 is viewed through specimen viewing region 227. In this embodiment, specimen region 227 includes the space from the sample to the detection optics. As shown, optical cavity 201 includes specimen viewing region 227. Although shown as a simple platform for simplicity of illustration, slide holder 223 optionally includes arms 225 for positioning slide 219, cutout regions for bottom mounted light or power sources, detection optics, or the like. In some embodiments, the slide and slide holder are integral.

Figure 3:
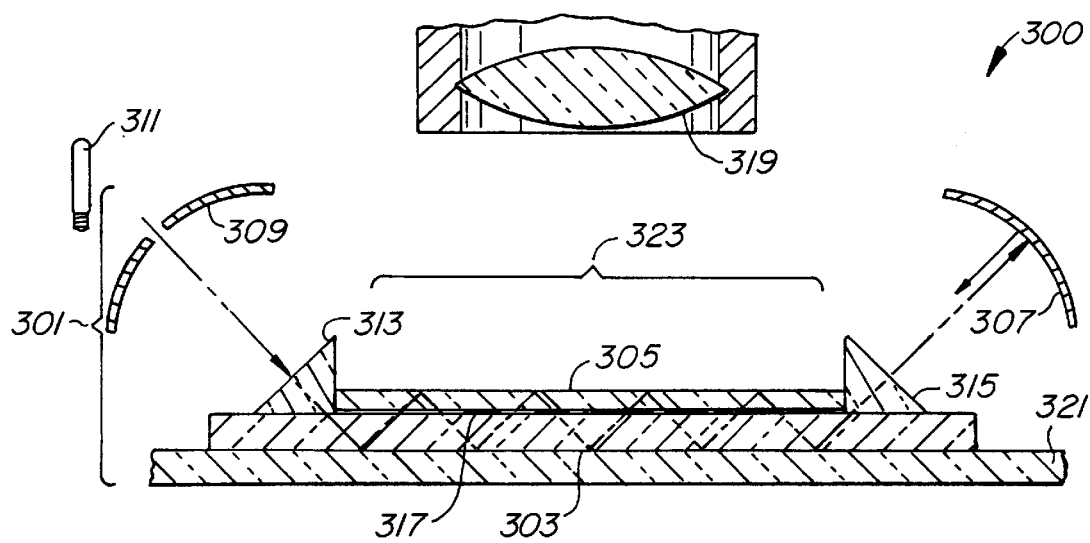
FIG. 3 is an illustration of an embodiment in which light is directed along the length of a sample slide using prisms and mirrors to achieve multiple passes of illumination light through the specimen.

FIG. 3 provides a third embodiment for the present invention. Apparatus 300 includes optical cavity 301 located between first reflective surface slide 303, second reflective surface coverslip 305 where reflections occur by total internal reflection, third reflective surface mirror 307 and fourth reflective surface mirror 309. Although depicted as curved, mirrors 307 and 309 are optionally flat. Appropriate curved mirror designs are hemispherical, hemieliptical, toroidal, or the like. Excitation light from input light source 311 enters optical cavity 301 through prism 313. Prism 313 allows light to efficiently enter slide 303, where it is reflected by total internal reflection from the lower surface of slide 303 or from a reflective coating on the tipper or lower surface of slide 303. The light can then undergo total internal reflection from the coverslip. After multiple reflections between slide 303 and coverslip 305, light travels through prism 315, and is reflected by mirror 307, back through prism 315, multiply reflected between coverslip 305 and slide 307, back through prism 313, onto mirror 309, and, again, back through optical cavity 301. Multiple passes of reflected light caused by travel of the light between mirror 307 and mirror 309 illuminates specimen 317 located between coverslip 305 and slide 303. Lens 319 detects light emitted or scattered by the specimen. Lens 319 collects scattered and/or fluorescent light as described in other embodiments, supra. Lens 319 can be a component of any known device for detecting an optical signal, including those described supra. Lens 319 is optionally located above or below the specimen. Slide 317 is held in position with slide holder 321 having slide viewing region 323. In this embodiment, slide viewing region 323 extends from specimen 317 to lens 319. Optical cavity 301 includes a portion of the specimen viewing region from slide 303 to coverslip 305. Optical cavity 301 includes slide 303, coverslip 305 and mirrors 307 and 309. As specimen 317 can be viewed from under slide 303 in embodiments where slide 303 is transparent, specimen viewing region 323 can also extend below slide 303 to a bottom mounted detector.

Although shown as a simple platform for simplicity of illustration, slide holder 321 optionally includes arms for positioning slide 303, cutout regions for bottom mounted light or power sources, detection optics, or the like. In some embodiments, the slide and slide holder are integral.

In one version of this embodiment, slide 303 is made, in whole or in part, from a reflective material, such as silver or aluminum, or includes a mirror finish. By making the surface highly reflective, the amount of fluorescence directed toward the detection optics is increased.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed.

In one preferred embodiment, hybridization to an array of biological polymers is monitored and recorded using a computer. One of skill is fully able to make arrays of biological polymers for viewing, and companies which specialize in the manufacture and design of such arrays are well known. Examples include Affymax, Inc. and Affymetrix, Inc., both of Santa Clara, Calif., and additional arrays are described in the art, e.g., in Pinkel et al. PCT/US95/16155 (WO 96/17958). It should be emphasized, however, that the apparatus and methods of the invention are easily used for illuminating any sample viewed by fluorescent or dark field microscopic techniques.

Accordingly, the disclosures and descriptions herein are intended to be illustrative, but not limiting, of the scope of the invention which is set forth in the following claims. All patents and publications cited herein are incorporated in their entirety for all purposes, as though each were individually indicated to be incorporated by reference.

What is claimed is:

1. An illumination apparatus, comprising:
   a specimen slide holder for mounting a specimen slide, the slide holder having a specimen viewing region;
   an optical cavity defined by a first reflective surface and a second reflective surface, the optical cavity being located adjacent the specimen slide holder and being further defined by a portion of the specimen viewing region;
   a light source for providing illumination light, wherein the light source is adjacent the optical cavity; and
   wherein the first and second reflective surfaces are arranged to produce multiple reflections of the illumination light within the optical cavity, thereby illuminating a portion of the specimen viewing region with multiple reflections of illumination light.

2. The apparatus of claim 1, wherein illumination light is reflected from the first reflective surface by total internal reflection.

3. The apparatus of claim 1, further comprising:
   a third reflective surface further defining the optical cavity and arranged to receive the reflected illumination light from the first reflective surface, and wherein the reflected illumination light is multipley reflected by the first reflective surface, the second reflective surface and the third reflective surface.

4. The apparatus of claim 1, further comprising:
a slide mounted in the slide holder, the slide having a specimen side, a light receiving side, and a specimen positioned on the specimen receiving side of the specimen slide; and,
a coverslip, comprising the first reflective surface, which coverslip covers a portion of the specimen.

5. The apparatus of claim 4, further comprising a prism positioned between the second reflective surface and the light receiving side of the specimen slide, the second reflective surface positioned to reflect the reflected illumination light through the prism, which prism directs the reflected illumination light through the light receiving side of the specimen slide and against the coverslip, which coverslip directs the reflected illumination light through the prism against the second reflective surface, which second reflective surface directs the reflected illumination light through the prism and against the coverslip.

6. The apparatus of claim 5, wherein the prism is mounted on the light receiving side of the specimen slide.

7. The apparatus of claim 6, wherein the prism is mounted on the light receiving side of specimen slide with an immersion oil.

8. The apparatus of claim 5, wherein the prism and the second reflective surface are integral.

9. The apparatus of claim 4, the apparatus further comprising a solution with an index of refraction greater than 1 on the specimen side of the specimen slide between the specimen side and the coverslip.

10. The apparatus of claim 4, wherein the specimen slide and the coverslip are planar and wherein illumination light which is not reflected by the coverslip exits the coverslip at an angle close to a plane defined by the coverslip.

11. The apparatus of claim 9, wherein the solution is a glycerol-based anti-fading solution with an index of refraction of about 1.5.

12. The apparatus of claim 1, further comprising a specimen slide, wherein the specimen slide comprises a specimen selected from the group consisting of an array of biological polymers, a rare cell, and a fluorescent protein.

13. The apparatus of claim 12, wherein the specimen is an array of biological polymers, and wherein the nucleic acid array and the specimen slide are integral.

14. The apparatus of claim 1, further comprising a specimen in the form of an array of biological polymers, wherein the polymers are deposited onto a solid substrate.

15. The apparatus of claim 1, further comprising a specimen in the form of an array of biological polymers, wherein the polymers are synthesized on the solid substrate.

16. The apparatus of claim 1, further comprising a specimen that comprises a fluorescent moiety.

17. The apparatus of claim 1, further comprising a specimen that is viewed by light scattering.

18. The apparatus of claim 1, wherein the second reflective surface is curved.

19. The apparatus of claim 18, wherein the second reflective surface has a shape selected from the group consisting of spherical and parabolic.

20. The apparatus of claim 1, further comprising a lens, which lens is mounted for collecting light from the specimen viewing region.

21. The apparatus of claim 20, further comprising a camera for obtaining an optical image of the specimen viewing region.

22. The apparatus of claim 20, further comprising a camera for obtaining an optical image of the specimen, wherein the camera is a CCD camera and the apparatus further comprises a data collection device for monitoring the optical image of the specimen.

23. The apparatus of claim 22, wherein the data collection device comprises a computer.

24. The apparatus of claim 1, wherein the illumination light from the light source is plane polarized.

25. The apparatus of claim 1, wherein the light source is an arc lamp, wherein the illumination light is transmitted to the optical cavity using a fiberoptic cable, which cable comprises an orifice in an end of the cable, which orifice is positioned in an aperture in a reflective surface of the apparatus.

26. The apparatus of claim 1, further comprising a specimen slide with a light reflecting side comprising the first reflective surface.

27. The apparatus of claim 26, further comprising:
a coverslip covering a portion of the light reflecting side of the specimen slide;
a specimen positioned on the specimen slide;
a first prism mounted on the specimen slide for directing illumination light from the light source against the light reflecting specimen side of the specimen slide;
the light reflecting specimen side of the specimen slide multiply reflecting a portion of the illumination light against the coverslip, which coverslip multiply reflects illumination light against the light reflecting side of the specimen side of the specimen slide, thereby illuminating the specimen with multiply reflected illumination light.

28. The apparatus of claim 27, further comprising a specimen that is mounted on the light reflecting side of the specimen slide.

29. The apparatus of claim 27, further comprising a second prism mounted on the specimen slide, which second prism directs multiply reflected illumination light against a first mirror, which mirror reflects the multiply reflected illumination light back through the second prism and against the light reflecting specimen side of the specimen slide, wherein the multiply reflected illumination light is reflected between the light reflecting specimen side of the specimen slide and the coverslip, thereby further illuminating the specimen.

30. The apparatus of claim 29, further comprising a second mirror mounted to reflect multiply reflected illumination light from the first prism back through the first prism against the light reflecting specimen side of the specimen slide, where the multiply reflected illumination light is reflected between the light reflecting specimen side of the specimen slide and the coverslip, thereby further illuminating the specimen, which second mirror comprises a light transmission aperture which permits illumination light from the light source to pass through the aperture.

31. The apparatus of claim 27, wherein the specimen slide and the specimen are integral.

32. The apparatus of claim 1, further comprising a reflective slide comprising the first reflective surface mounted in the slide holder, a specimen located on the reflective slide, and a coverslip comprising the second reflective surface, which coverslip covers a portion of the specimen, wherein illumination light from the light source is multiply reflected between the coverslip and the reflective slide.

33. The apparatus of claim 1, further comprising:
a first lower mirror for reflecting illumination light, comprising the first reflective surface, which first lower mirror is located below the specimen slide holder, which first lower mirror is positioned to reflect multiple passes of illumination light to the specimen holder; and, a first upper mirror for reflecting illumination light, comprising the second reflective surface, which first upper mirror is located above the specimen slide holder, which first upper mirror is positioned to reflect multiple passes of illumination light to the specimen holder;

wherein the illumination light from the light source is multiply reflected between the upper and lower mirrors to illuminate the specimen slide holder.

34. The apparatus of claim 33, further comprising a second lower mirror and a second upper mirror which are positioned to further multiply reflect illumination light from the first upper mirror or first lower mirror to further illuminate the specimen.

* * * * *